US008779389B2

(12) United States Patent
Allen et al.

(10) Patent No.: US 8,779,389 B2
(45) Date of Patent: Jul. 15, 2014

(54) DETECTION METHOD BASED ON WHISPERING GALLERY MODES IN MICROSPHERES FLOATING IN A SOLUTION UNDER TEST

(75) Inventors: Claudine Allen, Saint-Isidore (CA); Alex Paquet, Quebec (CA); Maxime Charlebois, Saint-Etienne (CA)

(73) Assignee: Universite Laval, Quebec (CA)

( * ) Notice: Subject to any disclaimer, the term of this patent is extended or adjusted under 35 U.S.C. 154(b) by 311 days.

(21) Appl. No.: 13/157,413

(22) Filed: Jun. 10, 2011

(65) Prior Publication Data

US 2011/0303856 A1    Dec. 15, 2011

Related U.S. Application Data

(60) Provisional application No. 61/353,439, filed on Jun. 10, 2010.

(51) Int. Cl.
*G01J 3/44* (2006.01)
*G01N 21/64* (2006.01)

(52) U.S. Cl.
USPC .................................. 250/458.1; 250/461.1

(58) Field of Classification Search
USPC .......................................... 250/458.1, 461.2
See application file for complete search history.

(56) References Cited

U.S. PATENT DOCUMENTS

| | | | |
|---|---|---|---|
| 6,490,039 B2 | 12/2002 | Maleki et al. | |
| 6,583,399 B1 | 6/2003 | Hunziker et al. | |
| 6,668,111 B2 | 12/2003 | Tapalian et al. | |
| 6,781,696 B1 | 8/2004 | Rosenberger et al. | |
| 7,259,855 B2 | 8/2007 | Fan et al. | |
| 7,271,379 B2 | 9/2007 | Fan et al. | |
| 7,352,933 B2 | 4/2008 | Fan et al. | |
| 7,384,797 B1 | 6/2008 | Blair | |
| 2004/0137478 A1* | 7/2004 | Arnold et al. | 435/6 |
| 2005/0032244 A1 | 2/2005 | Nie et al. | |
| 2006/0062508 A1 | 3/2006 | Guo et al. | |
| 2007/0114477 A1 | 5/2007 | Teraoka et al. | |
| 2007/0269901 A1 | 11/2007 | Armani et al. | |

FOREIGN PATENT DOCUMENTS

WO    2005116615    12/2005

OTHER PUBLICATIONS

Charlebois et al. "Toward Automatic Label-Free Whispering Gallery Modes Biodetection with a Quantum Dot-Coated Microsphere Population." Nanoscale Res Lett (2010) 5:524-532.*
Francois et al. "Whispering Gallery Mode Biosensor Operated in the Stimulated Emission Regime." Appl. Phys. Lett. (94) 031101:1-3 (2009).*
"Mie Theory." Wikipedia article accessed May 14, 2013. <http://en.wikipedia.org/wiki/Mie_scattering>.*

(Continued)

*Primary Examiner* — Casey Bryant
(74) *Attorney, Agent, or Firm* — Norton Rose Fulbright Canada LLP; Alexandre Dacust (57) ABSTRACT

The detection method can include: exciting at least one fluorescent microsphere floating in said solution under test by exposing it to excitation light; measuring a fluorescence spectrum of said at least one fluorescent microsphere, said fluorescence spectrum comprising multiple whispering gallery modes; obtaining a set of predetermined fluorescence spectra corresponding to those of microspheres having varying external refractive index and varying radius, identifying a matching fluorescence spectrum of the set which more closely matches the measured fluorescence spectrum; comparing the matching fluorescence spectrum of the set to the measured fluorescence spectrum.

10 Claims, 9 Drawing Sheets

(56) References Cited

OTHER PUBLICATIONS

M. Charlebois, A. Paquet, L.S. Verret, K. Boissinot, M. Boissinot, M.G. Bergeron, C. Ni. Allen "Toward Automatic Label-Free Whispering Gallery Modes Biodetection with a Quantum Dot-Coated Microsphere Population", Nanoscale Research Letters, 2010, vol. 5, No. 3, pp. 524-532, published online Feb. 20, 2010.

A. Paquet, "Statistical Analysis of Multiple Whispering Gallery Modes Resonances for Biodetection", Aug. 13, 2009, Oral presentation by Mr. Alex Paquet at the joint conference "14th Canadian Semiconductor Technology Conference/Nano and Giga Challenges in Electronics, Photonics and Renewable Energy".

A. Paquet, M. Charlebois, C. Allen, "Detection of Bacteria With Shifts of Whispering Gallery Modes Optical Resonances", Jun. 11, 2009, posted at <http://asdn.net/ngc2009/raw_abstracts//attached_abstracts/090401135900/abstract.pdf>.

\* cited by examiner

DETECTION METHOD BASED ON WHISPERING GALLERY MODES IN MICROSPHERES FLOATING IN A SOLUTION UNDER TEST

CROSS-REFERENCE TO RELATED APPLICATIONS

Priority is claimed from U.S. Provisional application 61/353,439 filed Jun. 10, 2010, the contents of which are hereby incorporated by reference.

BACKGROUND

Whispering Gallery Modes (WGM) in microspheres are optical resonances taking place in a microcavity having a cylindrical or spherical symmetry. These modes circulate at the edge of a microsphere by total internal reflection where they are affected by external perturbations via the evanescent field energy coupling.

Dielectric microspheres act as resonators with a geometry that offers the highest quality factor (Q up to $10^9$). Light trapped in these resonators by means of total internal reflection exhibits WGMs at specific wavelengths known from Mie theory. In this formalism, these resonances are determined by the radius a of the microsphere and the refractive index contrast m=m1/m0 where m1 and m0 are the refractive indices of the microsphere and the surrounding medium, respectively.

WGM detection requires no microbial culture. It has shown great sensitivity in monomolecular detection. The use of multiple microspheres having different targeted analytes, i.e. bacteria or viruses, allows for detection of multiple infectious diseases with a single analysis.

However, because even slight variations of the radius of the microspheres affect the WGMs and because it is not yet possible to manufacture microspheres with such tight precision, WGM refractometry requires pre-calibration of the WGM spectral displacements for each microsphere against a reference solution. It was therefore mandatory that measurements be carried out on the same microsphere before and after contact with a test solution including the analytes. The microsphere should therefore be fixed on a substrate throughout the test for the position of each microsphere to be retraceable. Fixing microspheres on a substrate however decreases sensitivity.

There is therefore a need for a technique allowing the WGM microbial detection with multiple microspheres targeting various analytes that may flow and move freely in the test solution.

SUMMARY

The whispering gallery mode resonance spectrum for given fluorophore wavelengths can be theoretically predicted for different radii and/or different indicia of refraction with a relatively high amount of precision. When detecting experimental spectra of microspheres floating freely in a solution, it was found that even when the spectrum is disturbed by external perturbations via the evanescent field coupling, it was possible by comparing the spectrum of selected ones of the microspheres to the predicted theoretical spectra to find a most closely corresponding match, thereby identifying a selected theoretical spectrum corresponding to the experimental spectrum of the microsphere under test, even though the size and indicia of refraction is not precisely known beforehand. Then, by comparing the experimental spectrum to the selected theoretical spectrum, it is possible to determine whether the experimental spectrum of the microsphere under test is affected by external perturbations. If the experimental spectrum is significantly different than the corresponding theoretical spectrum, one can conclude that it is affected by an external perturbation which is thus detected. The external perturbation can be an analyte on the external surface of the microsphere, for instance, or a liquid in the solution under test.

Bringing this concept to the next level, for detecting analytes, it is possible to use more than one set of microspheres, each set having distinct fluorophores and thus having distinct whispering gallery mode spectra. Each set can also be functionalized to attract only a specific type of analyte to be detected. Henceforth, the concept can serve to detect the individual presence or absence of more than one analyte in the solution under test.

Henceforth, there is provided a WGM-based sensing method that can omit calibration, reference measures or any prior knowledge about the microsphere radii. Only one spectrum acquisition per fluorescent microsphere is needed; hence, there is no need to keep track of the position of each microsphere between manipulations.

This opens up new engineering possibilities for sensor integration in fluidic systems (including microfluidics and lab-on-chip devices). In the case of biodetection, this method breaks free from surface-based sensing with poor analyte capture efficiencies and facilitates the mixing of microsphere sensors with analytes. Fitting a microsphere WGM measurement on a set of theoretical WGM spectra precalculated over the whole experimental spectral range ensures the finding of a unique combination (a, m0) of microsphere radius and refractive index of the surroundings corresponding to the WGM measurement. A satisfactory match is found between the theory, which takes into account the dipole emitters within the microspheres, and the experimental conditions, where the microspheres are in suspension.

Since free floating functionalized microspheres, which are now available commercially, may be directly used as fluorescent biodetectors, the sample preparation can be significantly simplified and shortened. The analyte is captured by an analyte targeting coating on the microspheres and detected without a reference measurement.

There is provided a WGM-based sensing method using various microspheres moving freely in the test solution and benefiting from a method using Instantaneous Measurement of the Apparent Refractive Index (IMARI) which releases the need to uses a comparative measurement. The use of in solution multiplexed microspheres provides good efficiency in capturing analytes and is compatible with flow cytometry analysis.

In accordance with one aspect, there is provided a detection method using Whispering Gallery Modes (WGMs) in microspheres floating in a solution under test. The method comprises exciting at least one fluorescent microspheres functionalized for targeted analytes and floating in said solution under test by exposing it to excitation light; measuring a fluorescence spectrum of said one of said fluorescent microsphere, said fluorescence spectrum comprising multiple whispering gallery modes; comparing the measured fluorescence spectrum with a set of predetermined fluorescence spectra, fluorescence spectra of the set corresponding to a various known external refractive index and various known radius of microspheres, in order to identify a matching fluorescence spectrum of the set which more closely match the measured fluorescence spectrum; determining an apparent external refractive index corresponding to said one of said fluorescent microspheres using said known external refractive index corresponding to the matching fluorescence spectrum; and determining a presence of targeted analytes attached to said one of said fluorescent microspheres as a function of at least the apparent external refractive index and a predetermined distribution of refractive index of said solution under test.

BRIEF DESCRIPTION OF THE DRAWINGS

It will be noted that throughout the appended drawings, like features are identified by like reference numerals.

DETAILED DESCRIPTION

Figure 8A:
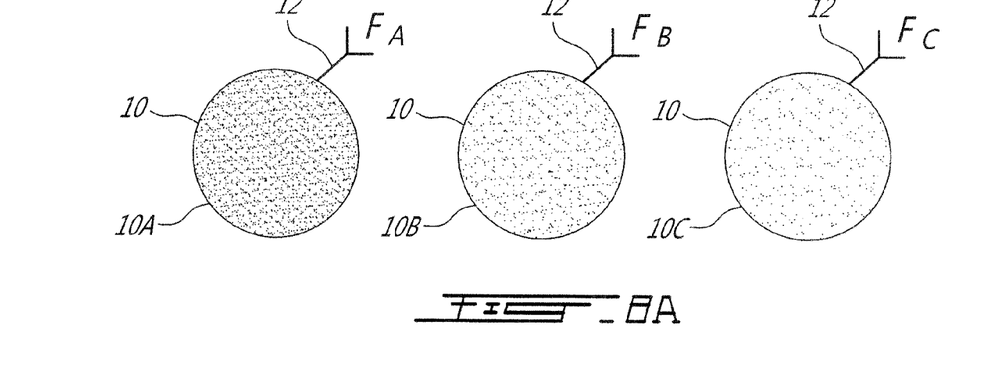
FIG. 8A is a schematic view illustrating functionalized microspheres.

Now referring to the drawings. FIG. 8A is a schematic view illustrating microspheres 10 to be used in the Whispering Gallery Mode (WGM) detection methods described herein. The WGM detection methods described herein use fluorescent microspheres 10 as optical cavities. The microspheres 10 are typically made of dielectric material such as polystyrene for example. They comprise inclusions of fluorescent molecules or fluorescent quantum dots, referred to herein generally as fluorophores. The fluorophores are used to excite the WGMs in the microspheres 10. Each microsphere 10 is also functionalized to a specific targeted analyte to be detected, represented as $F_A$, $F_B$ and $F_C$. This is made by applying on the microsphere 10 a coating which comprises receptors 12 adapted to bind to a specific targeted analyte, such as a specific bacteria or a specific virus. The receptors may be nucleotides, peptides, proteins, enzymes, antibodies, etc.

It is noted that although reference is made herein to biodetection, the methods described herein also apply to detection of analytes in general such as detection of chemical analytes and detection of particles.

Figure 9A:
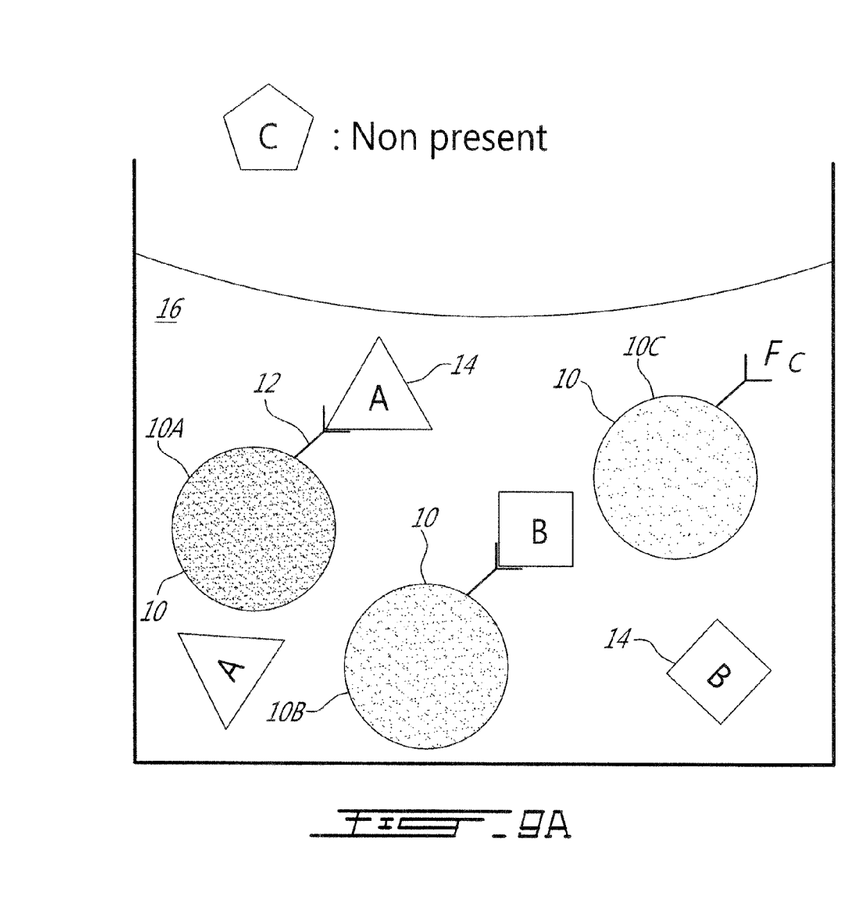
FIG. 9A is a schematic view illustrating microspheres floating in a solution under test in accordance with the method described herein.

As shown in FIG. 9A multiple microspheres 10 in the solution under test 16 constitute a population of detectors. The population of microspheres is typically a mixture of microspheres having different radii and different targeted analytes to allow multiplexed detection of various analytes 14, represented as A, B and C, in the same solution under test 16. The radius should however allow observation of WGMs in the fluorescence spectrum of the microspheres 10.

The microspheres 10 are mixed in the solution under test 16 and float freely to efficiently capture the targeted analytes 14.

The detection of the fluorescence spectrum of each individual microsphere 10, using a fluorescence microscope or a flow cytometry apparatus as known in the art, is indicative of the capture or not of an analyte on the microsphere 10. The presence of an analyte attached to the microsphere 10 changes the apparent external refractive index m0 as seen by the WGMs in the microsphere and consequently changes its fluorescence spectrum. As will be described below, using the measured fluorescence spectrum, it is possible to determine the external refractive index m0 as seen by the WGMs and thereby determine whether there is one or more analytes attached to the microsphere 10.

Figure 8B:
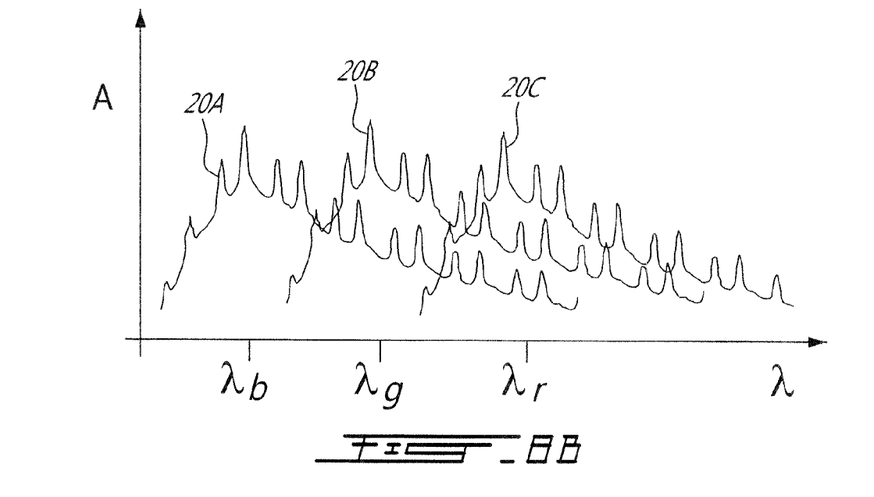
FIG. 8B is a graph illustrating the fluorescence spectrum of the microspheres of FIG. 8A in absence of analytes.

As shown in FIGS. 8A and 8B, in one embodiment, multiplexed detection of multiple analytes is made possible by associating a unique fluorescence wavelength λb, λg or λr to each analyte A, B, C to be detected. For example, microspheres 10A functionalized for detecting analyte A has a fluorophore emitting around wavelength λb which corresponds to blue light; microspheres 10B functionalized for detecting analyte B has a fluorophore emitting around wavelength λg which corresponds to green light; and microspheres 10C functionalized for detecting analyte C has a fluorophore emitting around wavelength λr which corresponds to red light. It is noted that any other fluorescence wavelength may be used, either in the visible or in the non-visible spectrum. Also, a population of microspheres 10A functionalized for analyte A may and typically comprises a mixture of microspheres with different radii.

FIG. 8B shows fluorescence spectra 20A, 20B, 20C respectively corresponding to microspheres 10A, 10B and 10C in absence of analytes. The peaks on the fluorescence spectra correspond to the WGMs which are modulated with the emission spectrum of the fluorophore in the microsphere. The peak wavelength λb, λg, λr of each fluorescent spectrum is determined by the fluorophore used in the microsphere. During detection, it can be related to the detected analyte 14 by the predetermined association between the targeted analytes A, B, C and peak wavelengths λb, λg, λr. It is therefore possible, from the measured fluorescence spectrum, to determine which analyte A, B or C is being detected by a specific microsphere 10, by identifying the peak wavelength of the measured fluorescence spectra.

Figure 9B:
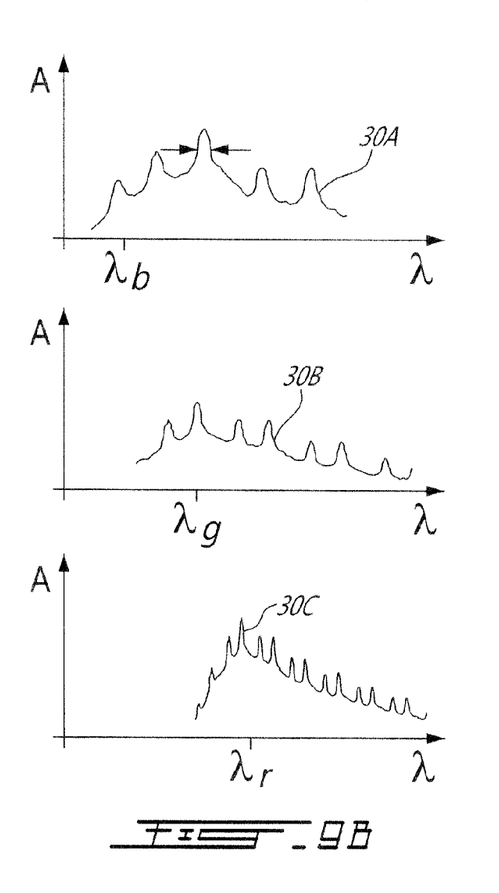
FIG. 9B is a graph illustrating the fluorescence spectrum of the microspheres of FIG. 9A where some microspheres have analytes attached thereto.

A detection method using WGMs is now described with reference to FIGS. 9A and 9B.

The WGMs on the fluorescence spectrum of a microsphere 10 are a function of the refractive index m1 of the microsphere 10, the refractive index m0 external to the microsphere 10 which changes according to the presence or not of analytes attached to the microsphere 10, and the radius a of the microsphere 10. The refractive index m1 of the microsphere 10 is typically known. However, because the population of microspheres 10 has variable and unpredictable radii, each microsphere 10 has a radius a that is unknown. The external refractive index m0 is also unknown as it varies with the presence of not of analytes 14 attached on the microsphere 10. Accordingly, each microsphere 10 has a fluorescence spectrum which is characteristic. It is the measure of the external refractive index m0 that allows for determining the presence of analytes 14.

It has been found that it is possible to theoretically predict with accuracy the fluorescence spectrum of a microsphere when knowing its radius a, its refractive index m1 and the external refractive index m0, i.e. of the surrounding homogenous medium. This can be done using the Mie theory as described in H. Chew, Phys. Rev. A38, p. 3410 (1988) and H. Chew, J. Chem. Phys. 87, p. 1355 (1987).

It has also been found that when knowing the refractive index m1 of a microsphere, its fluorescent spectrum is unique to a specific pair (m0, a) of external refractive index m0 and radius a. Accordingly, by knowing the characteristic fluorescence spectrum of a microsphere, it is be possible to retrieve those parameters.

Accordingly, preliminarily to the detection method provided herein, theoretical fluorescent spectra of microspheres to be used in the detection are calculated. A set of a plurality of theoretical fluorescent spectra corresponding to a variety of known pair (m0, a) of external refractive index m0 and radius a are calculated and used as references. As will be explained herein below, this set of fluorescent spectra is later used in the detection to determine the pair (m0, a) of external refractive index m0 and radius a of the microsphere under test.

When a microsphere has no analyte attached, the external refractive index m0 corresponds to the refractive index of the surrounding homogenous medium. In presence of analytes attached to the surface of the microsphere, the external refractive index m0 as seen by the WGMs is altered by the presence of analytes. The external refractive index m0 then saw by the WGMs is said to be apparent because it does not correspond to the homogenous case as considered in the theoretical analysis. It rather corresponds to an effective value determined by the local variation of refractive index caused by the presence of one or more analytes.

Accordingly, the presence or not of analytes attached to the microsphere under test is determined by comparing a determined apparent external refractive index m0 of the microsphere to the external refractive index m0 corresponding to the refractive index of the surrounding homogenous medium, i.e. as seen by a microsphere having no analyte attached.

The method provided herein does not require a comparative measurement on the exact same microsphere before and after contact with the analytes. However, a threshold on the apparent external refractive index m0 for the detection for analytes should be determined.

This threshold is determined using WGMs in microspheres floating in a reference solution. Fluorescence spectra are measured on microspheres having no analyte attached. These measurements are used to determine the external refractive index m0 that is expected in the case of homogenous solution, i.e. with no analyte. The reference solution should be representative of the solution under test in which analytes are to be detected, i.e. it should have the same refractive index. Two example methods are provided herein for providing the reference solution.

In a first embodiment, a part of the solution under test is taken out from original solution and filtered or otherwise processed to remove analytes therefrom and provide a reference solution. A population of microspheres in then mixed in the reference solution and fluorescent spectra of the microspheres are measured. An external refractive index m0 of the homogenous medium is determined using the set of predetermined fluorescence spectra for each tested microsphere as explained in more details below. Variations on the external refractive index m0 are typically seen, which are due to defaults such as damaged microspheres, non-uniform functionalizing coating, temperature fluctuations in the solution, etc. A distribution of external refractive index m0 is than observed and a threshold on the external refractive index m0 above which an analyte is considered is determined.

In a second embodiment, a part of the solution under test is taken out from original solution and is used as a reference solution. A population of microspheres made without functionalizing coating is mixed with the reference solution and fluorescent spectra of the microspheres are measured. Microspheres without functionalizing coating can intrinsically repel analytes or short interactions with the analytes average to emulate a homogenous case. The distribution of external refractive index m0 is observed as above and the threshold to be later used in the detection is determined.

Having determined the set of a plurality of theoretical fluorescent spectra corresponding to a variety of known pair (m0, a) and the detection threshold on the apparent external refractive index m0, a detection method using Whispering Gallery Modes in microspheres floating in a solution under test is as follows.

A population of fluorescent microspheres functionalized for targeted analytes are mixed with the solution under test containing analytes to be detected. The microspheres float freely in the solution. The population of microspheres typically comes from the same batch of the ones used on the reference solution. Analytes present in the solution under test bind with microspheres that are functionalized specifically for these given analytes (see FIG. 9A).

The microspheres are then excited by exposing them to excitation light in order to produce a fluorescence spectrum.

The fluorescence spectra of a plurality of microspheres in the solution under test are then measured one microsphere at a time. This may be done for example using a fluorescence microscope or a flow cytometer as known in the art. It is noted that the measure should cover a multitude of WGMs.

Each measured fluorescence spectrum is compared with the set of predetermined fluorescence spectra, in order to identify a matching fluorescence spectrum of the set which more closely match the measured fluorescence spectrum.

Indicators of the presence of an analyte on the microsphere under test are then determined using the matching fluorescence spectrum. The presence of targeted analytes attached to the microsphere under test is determined considering the indicators. If these indicators are above the predetermined threshold, this measurement is considered to correspond to a detection event.

In one embodiment, the indicator used for determining the presence or not of analytes is the apparent external refractive index m0 of the microsphere. The apparent external refractive index m0 of the microsphere is determined by knowing the external refractive index m0 corresponding to the matching fluorescence spectrum. If the determined apparent refractive index m0 is above the predetermined threshold, this measurement is considered to correspond to a detection event. In one embodiment, the threshold is determined as a function of the distribution of refractive index as measured on the reference solution, and corresponds to three times the standard deviation of the distribution of refractive index measured on the reference solution. Other thresholds may be used as well, such as two times the standard deviation for example.

The same is performed on a plurality of microspheres. It is noted that the number of detection events is a function of the number of analytes captured by the microspheres which is function of the concentration of analytes in the solution under test, of the concentration of microspheres functionalized for the analytes and of the efficiency of capture by the microspheres.

Of course, instead of the threshold being based for example on three times the standard deviation, a more complex statistical analysis as known in biodetection may be performed.

It is noted that in the case of multiplexed detection as described herein above, an additional step of determining the specific analyte A, B or C targeted by the microsphere under test should be introduced. This can be simply made by measuring the peak wavelength of the measured fluorescence spectrum and comparing it to the known peak wavelengths $\lambda b$, $\lambda g$, $\lambda r$ associated with the targeted analytes A, B, C.

It is noted that multiplexed detection may also be provided by associating different microsphere radius ranges to different types of analytes instead of the association with the peak wavelength of the fluorescence spectrum of the microsphere. Accordingly, a first population of microspheres is provided in a first range of radii, 9 μm+/−0.2 μm for example. This first population is functionalized to target a first analyte A. A second population of microspheres is provided in a second range of radii, 9.5 μm+/−0.2 μm for example. This second population is functionalized to target a second analyte B. A third population of microspheres is provided in a third range of radii, 10.0 μm+/−0.2 μm for example. This third population is functionalized to target a third analyte C. The first, the second and the third populations are mixed together and mixed in the solution under test. The first, second and third ranges of radii should not overlap in order to allow differentiation between the microspheres of each population. It is noted that the number of analytes that can be multiplexed depends on the radius tolerance of the microspheres that is achievable by the microsphere manufacturers. In order to differentiate microspheres targeting different analytes, the radius of each microsphere under test is determined using the known radius associated with the matching fluorescence spectrum and comparing the determined radius with the known ranges of radii associated with each analyte.

In another embodiment, a combination of the radius of the microsphere and the peak wavelength of the fluorescence spectrum of the microsphere is associated with each type of analytes to be detection for use in multiplexed detection.

Experimental results obtained using the detection methods described herein are now given.

Fluorescent Microspheres:

To determine the absolute value of the solution refractive index m0 and microsphere radius a, multiple WGMs should be measured at the same time, as will be discussed later. A wide spectrum can be used. The spectra from fluorophores embedded in microspheres can easily cover more than 100 nm. The emitted light from these microspheres is coupled more strongly into the WGMs, but the original Mie theory fails to correctly predict the scattered emission spectrum. This theory predicts the right WGM resonance wavelengths, but their relative intensity is better described by an Elaboration of Mie Theory (EMT) formulated in H. Chew, Phys. Rev. A38, p. 3410 (1988) and H. Chew, J. Chem. Phys. 87, p. 1355 (1987). Simulations were performed based on this theory to find a suitable wavelength range and microsphere radius producing well-defined WGM resonances. These simulations were carried out with Matlab R2007a for Windows on a personal computer. EMT showed that increasing the radius of microspheres and the light frequency improves the Q factor. Since this factor is contravariant with free spectral range, a compromise is needed to maximize both. The 0.5-nm resolution of the spectrometer used limits the resolving power to distinguish two consecutive WGMs. The free spectral range should thus be wide enough to resolve experimentally every single WGM over the whole spectral range chosen. However, we should also keep the Q factor sufficiently high for good sensing precision. Based on these considerations and the commercial availability of water-soluble fluorescent polystyrene microspheres, we chose product G1000 (Duke Scientific Corporation) with a nominal radius of 4,950 nm and emission centered around 520 nm. The Q factor of these microbeads was measured with an Andor CCD camera and spectrometer having a resolution of 0.1 nm. This value is smaller than the Full Width Half Maximum (FWHM) of the WGM peaks giving a Q factor of ≈2000.

Figures 3A, 3B, 3C:
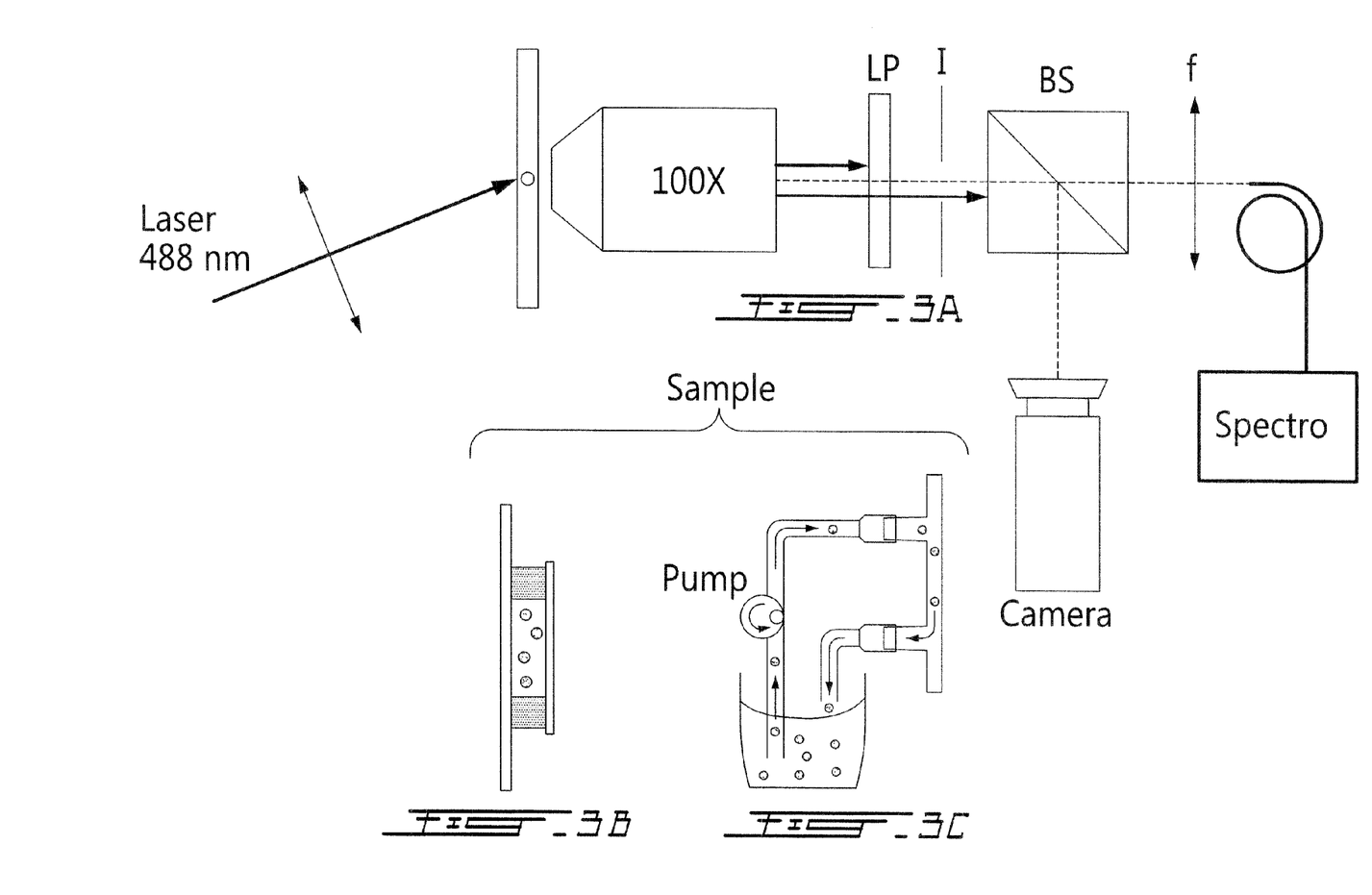
FIG. 3A is a schematic view illustrating an experimental setup used with the detection method described herein.
FIG. 3B is a schematic view illustrating a sealed chamber mounted on a microscope slide used in the experimental setup of FIG. 3A.
FIG. 3C is a schematic view illustrating a peristaltic pump used to circulate the solution under test on the microscope slide of FIG. 3B.

Experimental Setup:

The core of our experimental setup reproduces a typical fluorescence microscope as illustrated in FIG. 3A. However, the configuration is not the usual epifluorescence one. The 488-nm argon laser beam, exciting the fluorescent microspheres, is transmitted through the microscope slide making an angle with the fluorescence propagation axis, so that only scattered laser light will co-propagate with the fluorescence. A 100× immersion oil microscope objective Olympus UPlan-FLN100XO2, collects the fluorescence on the other side of the slide, and a long-pass filter blocks the scattered laser light. The green fluorescence continues through a variable diaphragm that isolates the emission of a single microsphere. A beam splitter sends a portion of this emission to a camera to visualize the microsphere, and the remainder is injected into a fiber spectrometer Ocean Optics USB4000 to record the fluorescence spectrum modulated by amplified WGMs. Two types of reservoir for fluids with microsphere sensors were used. The first tests were made with a SecureSeal™ SA8R-1.0 chamber bonded on a microscope slide as illustrated in FIG. 3B. This sealable chamber was filled with 60 μl of a given solution. The typical sensor concentration in the solutions was around 950 microspheres/µl, since this was a good compromise to facilitate the measurement process. Single microspheres flowed frequently within the focal spot of the objective without touching the slide, but the probability of seeing multiple ones at the same time was still low. The second type of reservoir was a complete microfluidic apparatus, as shown in FIG. 3C. A peristaltic pump Watson-Marlow 400 circulated the solution in a closed loop including an Ibidir® µ-Slide inserted in the optical setup. This slide has a 0.4×3.8×17 mm channel engraved with a≈170 µm thick wall on the imaging side. In this configuration, we can add, during same experiment, specific volumes of alcohols to vary the solution refractive index or add analytes at different concentrations to test the microspheres for biodetection.

Figure 1A:
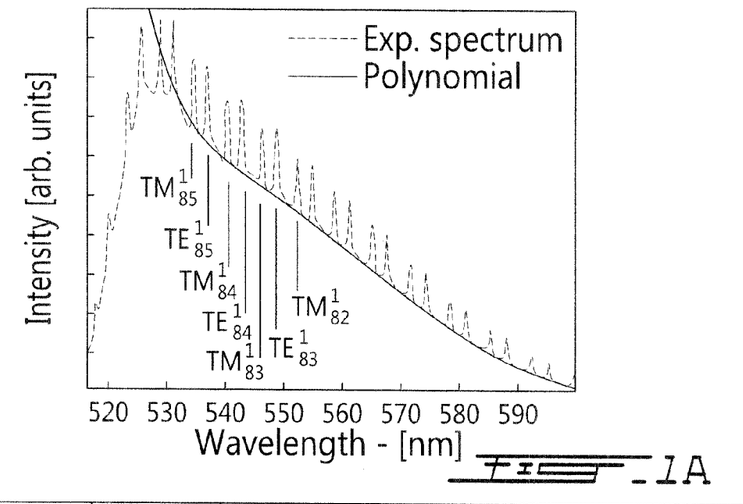
FIG. 1A is graph showing a smoothed fluorescence spectrum of a G1000 microsphere immersed in water (broken line), with the dark line indicating the polynomial used for background subtraction.
Figure 1B:
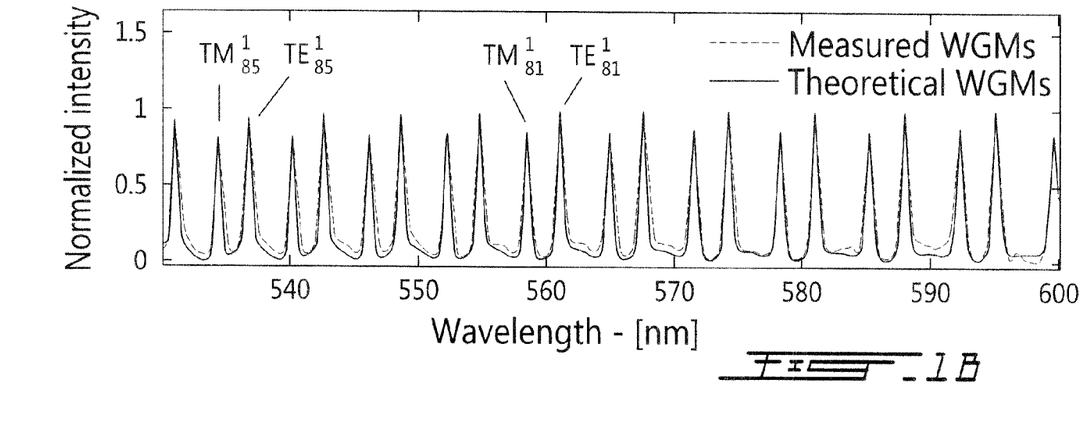
FIG. 1B shows the smoothed fluorescence spectrum of FIG. 1A with the substraction (broken line) superposed to a theoretical spectrum (dark line) calculated with Elaboration of Mie Theory (EMT calculated) displaying the agreement between theory and experiment.

Analysis Algorithm:

Before comparing it with EMT, the acquired WGM spectrum of each single fluorescent microsphere should first be processed. After noise filtering, a seventh-order polynomial is fitted to the spectrum baseline to determine the fluorescence intensity, and then it is subtracted from the spectrum (see FIG. 1A). The resulting spectrum is then divided by the same polynomial in order to normalize the intensity of each WGM. The resulting spectrum spans 70 nm centered at 565 nm as seen in FIG. 1B and is now ready to be compared to EMT predictions. Several theoretical spectra are calculated with Matlab algorithms in order to match the processed experimental spectrum. A typical least square algorithm cannot work automatically for multiple sharp peaks (such as WGMs) spectra, since it is an unstable procedure that usually requires a huge number of starting attempts to find the correct minimum. In order to proceed with such a fitting method, the starting parameters should thus be accurately determined first by a systematic, well-sampled rough scan of the parameter space. More precisely, a set of theoretical spectra is generated from EMT calculations for an ensemble of (a, m0) parameters. The refractive index of polystyrene is known and given by the Sellmeier relation $m1=1.5663+0.00785/\lambda^2+0.003478/\lambda^4$ (from Duke Scientific Corporation) where $\lambda$ is the wavelength in nanometers. This set of theoretical spectra covers values of radius a from 4,800 to 5,000 nm and values of m0 from 1.32 to 1.42 sampled at $\Delta a=0.1$ nm and $\Delta m0=0.0001$. Each calculated EMT spectrum associated to a (a, m0) coordinate is sufficiently sampled in wavelength ($\Delta\lambda=0.02$ nm) to avoid incomplete delineation of sharp WGM peaks. A convolution with the instrumental line shape (FWHM=0.5 nm) is then used to obtain a resolution matching the experimental data. This way, the energy contained in the extremely sharp WGMs is redistributed in a larger, shorter, Voigtian-like line profile, comparable with the experiment.

Figure 2A:
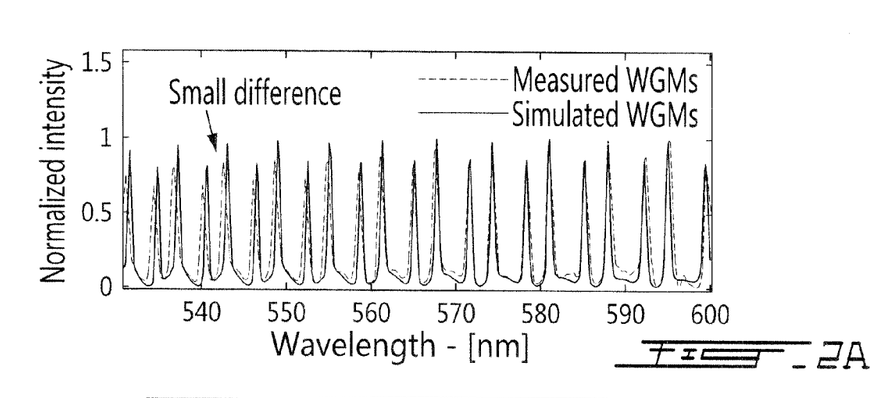
FIG. 2A is a graph showing an experimental spectrum disturbed by external perturbations, superposed to the theoretical spectrum (dark line), where the difference is a sign of the external perturbations.
Figure 2B:
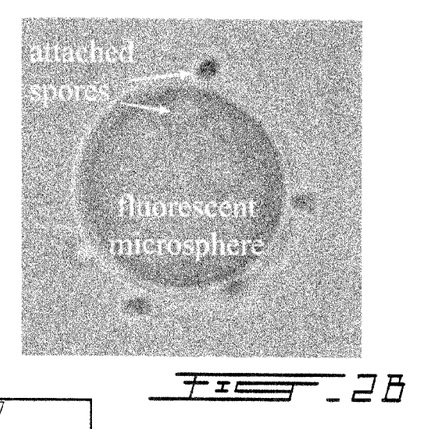
FIG. 2B is an image of a microsphere in water with spores adsorbed, acting as external perturbations.
Figure 2C:
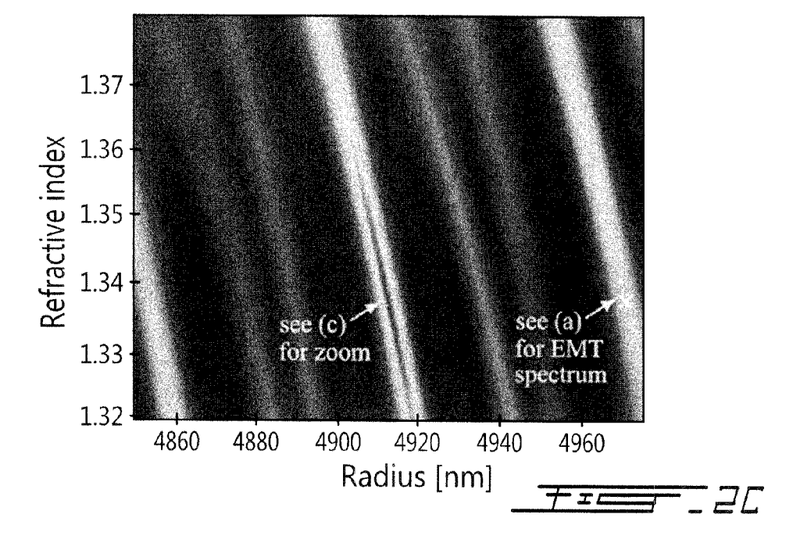
FIG. 2C is a contrast enhanced $\chi^2$ map of theoretical spectra compared to the experimental spectrum (EMT spectrum) of FIG. 2A with the absolute minimum and zoomed in FIG. 2D.
Figure 2D:
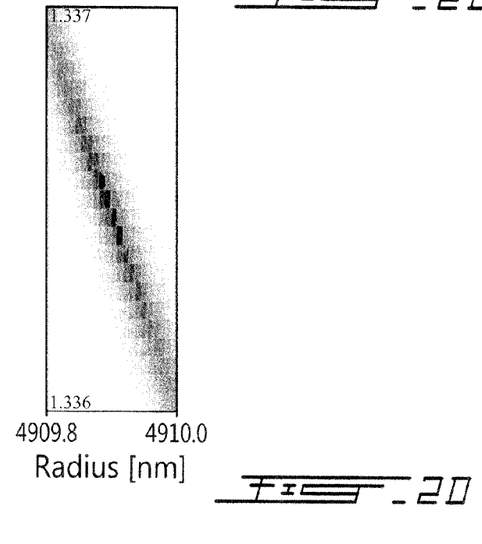
FIG. 2D is a zoom of FIG. 2C on the absolute minimum.

The processed experimental spectrum can now be compared to each calculated EMT spectrum with the least square approach. Calculating the squared sum of residuals between these spectra for each (a, m0) generates a $\chi^2$ map. FIG. 2C shows the global behavior of this map. Measuring and analyzing a single WGM peak would not yield the absolute minimum seen in this figure. Instead, we would obtain an infinite number of equivalent local minima with no possible distinction between them. The distinction becomes clear with 20 WGMs since the absolute minimum observed is a factor 2 lower than any other local minima, making the solution parameter set (a*, m0*) unique, see the zoom on this absolute minimum in FIG. 2D. The origin of this distinction is presented in FIG. 2A that corresponds to the EMT spectrum calculated 60 nm away in radius from (a*, m0*). The spectral stretch induced by such a radius change causes the overall WGM pattern to be shifted on average by the distance between $TM_l$ and $TM_{l+1}$ WGMs where l is the azimuthal mode number. When comparing theoretical versus measured spectra in FIG. 2A, it is apparent that not all WGMs are accurately superposed in the full spectral range whereas the same comparison at (a*, m0*) shown in FIG. 1B is near perfect. This ideal agreement is a consequence of working with EMT, which provides a more suitable formalism for fluorescent microspheres, and of our experimental conditions where the suspended microspheres do not lie on a substrate, hence m0 is truly homogeneous. Since the microsphere sample is polydisperse, no initial guess can be made about the radius coordinate a. Now that the initial rough scan has provided starting parameters very close to the absolute minimum, this fit can then be refined with a Levenberg-Marquardt algorithm (see D. Marquardt, SIAM 11, 431 (1963)) around (a*, m0*) since the smooth $\chi^2$ variation defines a relatively precise minimum. In order to converge to the absolute minimum, it has been noted that only one parameter should be fitted with the Levenberg-Marquardt algorithm. To do so, we fit only the radius a on a grid of m0 which is 10 times more precise than the initial scan. The overall method converges automatically every time with near perfect agreement as can be seen in FIG. 2D.

Refractive Index Sensing:

To test the accuracy of our method, we prepared solutions of microspheres in de-ionized (DI) water. Care was taken to remove the surfactants of the commercial solution by repeated centrifugation and resuspension. The resolution of the technique was evaluated from the standard deviation of (a*, m0*) measured with 10 consecutive spectra taken on the same microsphere and yielded 0.1 nm for a* and 0.0003 for m0*. Our technique was then applied on 100 different microspheres in DI water, and the measured refractive index was 1.3367±0.0003 with radiuses ranging from 4,860 to 4,980 nm. In this case, the uncertainty on m0* has been estimated by bootstrapping on 10 groups of 10 samples; its value being the same as the single microsphere case, it shows the ergodicity of the sensor. The mean difference from the theoretical value of water (1.3325±0.0001) is then used as a constant offset to correct for a systematic error that likely comes from omitting the variation of m0 with wavelength. This new sensor is now tested as a refractometer in FIG. 6 on water-ethanol and water-isopropanol solutions at different concentrations. Each point represents the average of 50 measures and is compared with reference curves. At low alcohol concentration, the reference curves fall within the 99.7% confidence interval of our data points. However, there is a systematic deviation for higher alcohol concentrations. Though degradation in precision can be expected in this latter case due to a lower refractive index contrast at the microsphere/solution interface reducing the visibility of the WGMs, we attribute the deviation mostly to the interaction of the polystyrene microsphere with its environment, since the alcohol can penetrate the microsphere and affect its optical properties. Swelling of polystyrene can occur as well in solutions with higher alcohol content, but this effect is accounted for independently by the algorithm adjusting automatically to the larger microsphere radius. Our demonstration of the technique here relies on convenient commercial microspheres as sensors that are not yet entirely optimized to reach the best resolution, thus work on the microcavity design is needed before comparing with the resolution of other sensors.

Biodetection:

A different and promising application to this new technique is high capture cross section biodetection. Since microspheres are negatively charged with a zeta potential measured to be around −60 mV, they should be covered by a poly-L- lysine polymer in order to attract negatively charged analytes such as spores and bacteria. Purified *Bacillus atrophaeus* subsp. *globigii* (referred to hereafter as simply *B. globigii*) spores were prepared and counted as previously described in F. J. Picard et al., J. Clin. Microbiol. 47, 751 (2009). These spores have an elongated shape with dimensions of approximately 2 by 1 μm. They are shown in FIG. 2B on a microsphere as observed with a 100× microscope objective. The spores were centrifuged from their PBS solution and resuspended in DI water at concentrations between $6.6 \times 10^{-15}$ M ($3.9 \times 10^6$ spores/ml) and $3.3 \times 10^{-12}$ M ($1.9 \times 10^9$ spores/ml). We emphasize that no measures were taken on the microspheres prior to mixing them with *B. globigii* spores. The signal transduction mechanisms for biodetection here are not the experimental variations in the WGM spectrum of a single microsphere starting from an initial analyte-free solution as done commonly. Instead, we seek departures from the ideal case considered by the EMT, i.e., a perfectly spherical and evenly fluorescent microsphere within a homogeneous medium. Indeed, spores adsorbed on microspheres, or otherwise located within the evanescent field region (referred to hereafter as analyte capture), will perturb the WGM propagation in a more local manner than a homogeneous change in m0. The fitting algorithm will partially adapt to this perturbation by adjusting (a*, m0*) which will no longer represent the microsphere radius and refractive index of water; hence in presence of analytes, we label (a*, m0*) as apparent radius and apparent refractive index respectively. Nonetheless, the quality of the fit deteriorates as indicated in FIG. 2A by the higher absolute minimum $\chi^2$ values we obtained, and this, in itself, is already an indicator that an inhomogeneous perturbation, not taken into account in our current model, occurs due to the *B. globigii* spores.

Figure 5A:
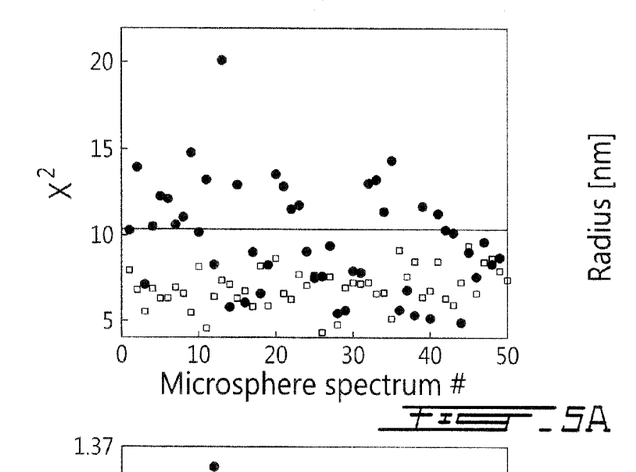
FIG. 5A is graph showing a goodness of fit $\chi^2$ values.
Figure 5B:
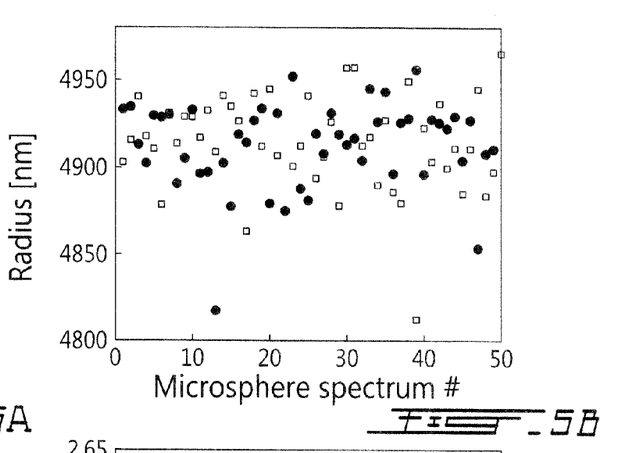
FIG. 5B is a graph showing the microsphere apparent radii.
Figure 5C:
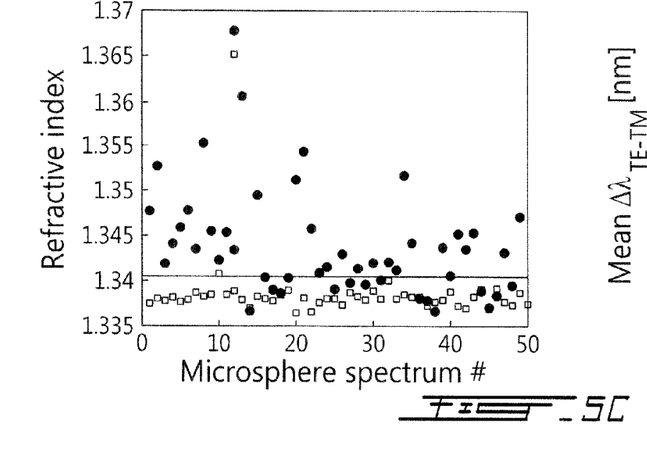
FIG. 5C is a graph showing the apparent refractive indexes of the microspheres.

Since the microsphere polydispersity hides the shift of apparent radius caused by the spores, FIG. 2C, we investigate the behavior of the apparent refractive index instead. FIG. 5C shows the values obtained from 50 microspheres in the $3.3 \times 10^{-12}$ M solution of *B. globigii* spores. We readily see that most of these values are significantly different from the refractive index of water. We also present in FIG. 5C are the refractive indexes measured with 50 microspheres in a spore-free control sample containing poly-Llysine coated microspheres in DI water that approach the ideal EMT case. This control sample allows us to estimate the effect of random fluctuations in experimental conditions, such as the thickness and surface roughness of the polymer coating, temperature, etc. These fluctuations also introduce departures from the ideal EMT case, but most of the apparent refractive indexes measured in the solution with spores are greater than the values from the control. This is in sharp contrast with the apparent radii values of FIG. 5B that fluctuates in the same manner for both solutions due to the microsphere polydispersity. Our method thus successfully detects the presence of *B. globigii* spores and not only experimental artefacts, this without any requirements on the microsphere polydispersity.

Figure 5D:
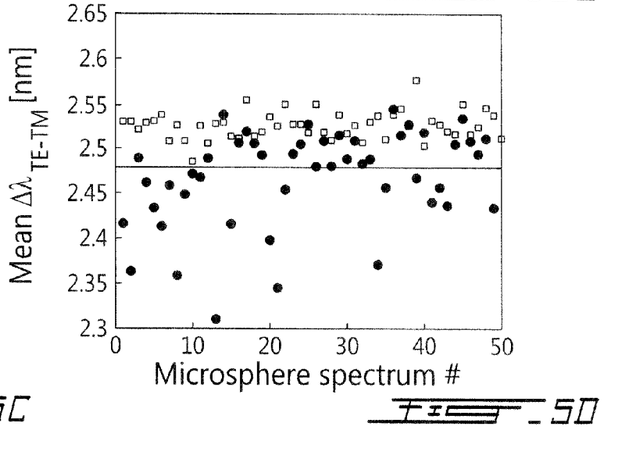
FIG. 5D is a graph showing the mean TE-TM mode spacing obtained from EMT fit on the WGM spectra of 50 fluorescent microspheres labeled on the x axis, wherein the solid dots are for a 3.3E-12 M (1.9E9 spores/mil) solution of $B.$ $globigii$ spores, wherein the open squares are for the control sample in DI water, and wherein the line represents the threshold (3σ, 99.7% confidence interval) for biodetection occurring above the line in FIG. 5A and FIG. 5C, but below in FIG. 5D.

Going back to the EMT fitted spectrum, we can seek for a characteristic of the WGMs that isn't too sensitive to the randomly fluctuating microsphere radius but yet known to be correlated to the refractive index in the ideal homogeneous case. The spacing in wavelength between $TE_l$–$TM_l$ modes was shown to be such a characteristic, and we calculated its mean value for the l≈76 to l≈85 modes (mean $\Delta\lambda_{TE-TM}$) in our EMT fitted spectra. The results are shown in FIG. 5D for both the $3.3 \times 10^{-12}$ M solution of *B. globigii* spores and the control sample. We combined the panels (c) and (d) of FIG. 5 into a new one: each point in FIG. 6 corresponds to a single microsphere EMT fitted spectrum whose coordinates are its apparent refractive index (x axis) and its mean TE-TM mode spacing (y axis). The anticipated correlation between both fitted parameters is clearly seen with some dispersion similar to the one observed for the control sample. The wider spread along the vertical direction is attributed to fluctuations in microsphere radii but is limited by the <5% polydispersity stated by the manufacturer. Many other characteristics of the WGMs can be investigated to find the most relevant indicators of biodetection.

Interestingly, the solution with spores yields an elongated spread of data points. A possible interpretation for this elongation is that its (m0, mean $\Delta\lambda_{TE-TM}$) coordinates are related to the number of spores on a single microsphere. Data points in FIG. 6 with lower apparent refractive index, and its associated higher mean TE-TM mode spacing, are closer to the control sample and thus might correspond to fewer spores adsorbed on the microsphere. Conversely, data further away in the lower right of the graph are likely to represent microspheres with a greater number of adsorbed spores. This seems to be confirmed when we compare the elongation for two different spore concentrations in FIG. 7. The cloud of data points is less stretched out, more clustered in the upper left of the graph, when the solution contains fewer spores per unit volume consistent with a smaller number of spores adsorbed per microsphere.

Figure 6:
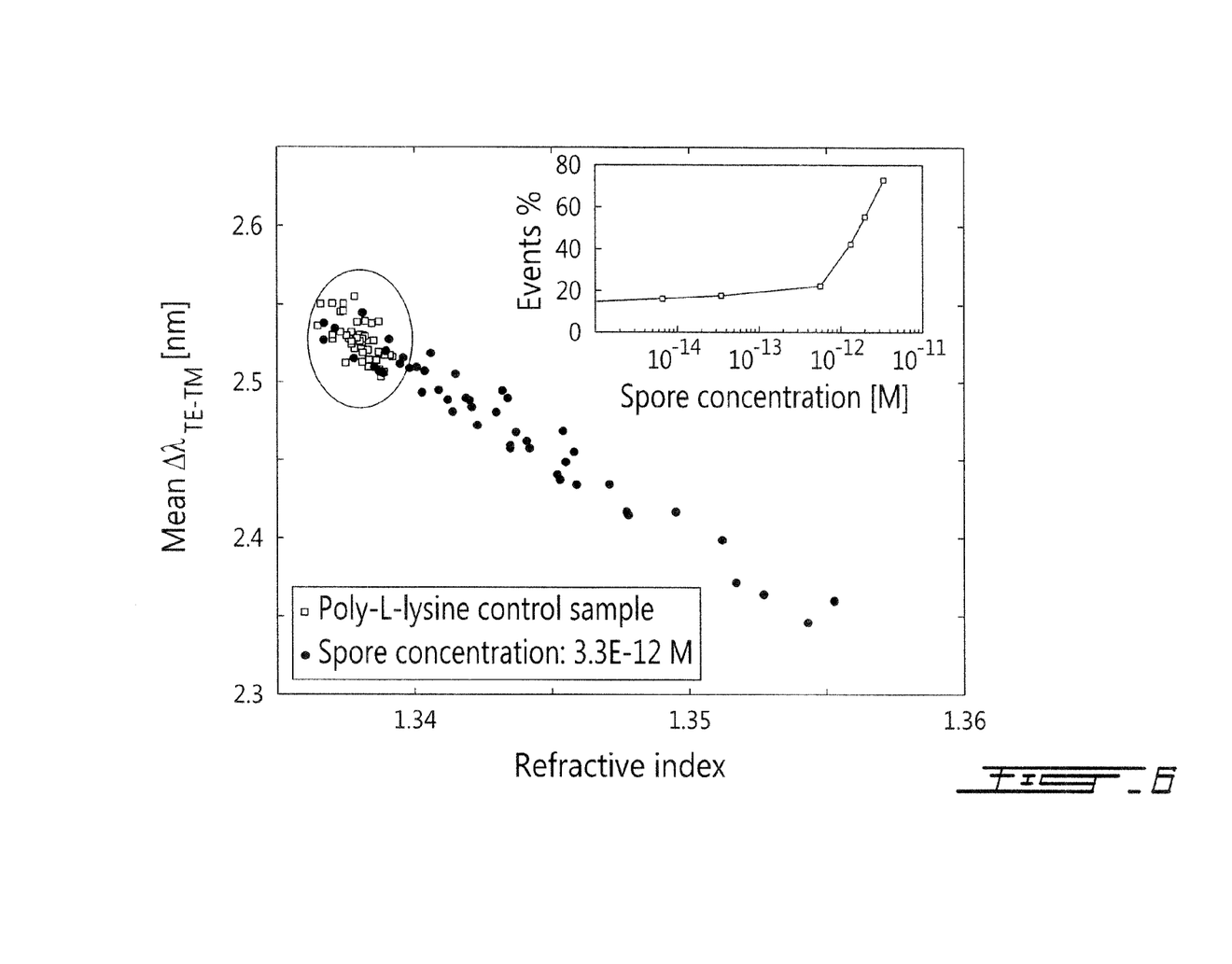
FIG. 6 is a graph showing data of FIG. 5A to FIG. 5D for the 3.3E-12 M solution of spores and the control sample, but presenting the apparent refractive index on the x axis and the mean TE-TM spacing on the y axis to put emphasis on the correlation, wherein the ellipse corresponds to the threshold set at three standard deviations of the control sample distributions, beyond which a data point is considered as a biodetection event, and wherein the graph inset shows the biodetection event percentage for distribution of 50 measurements at different concentration of $B.$ $globigii$ spores.
Figure 7:
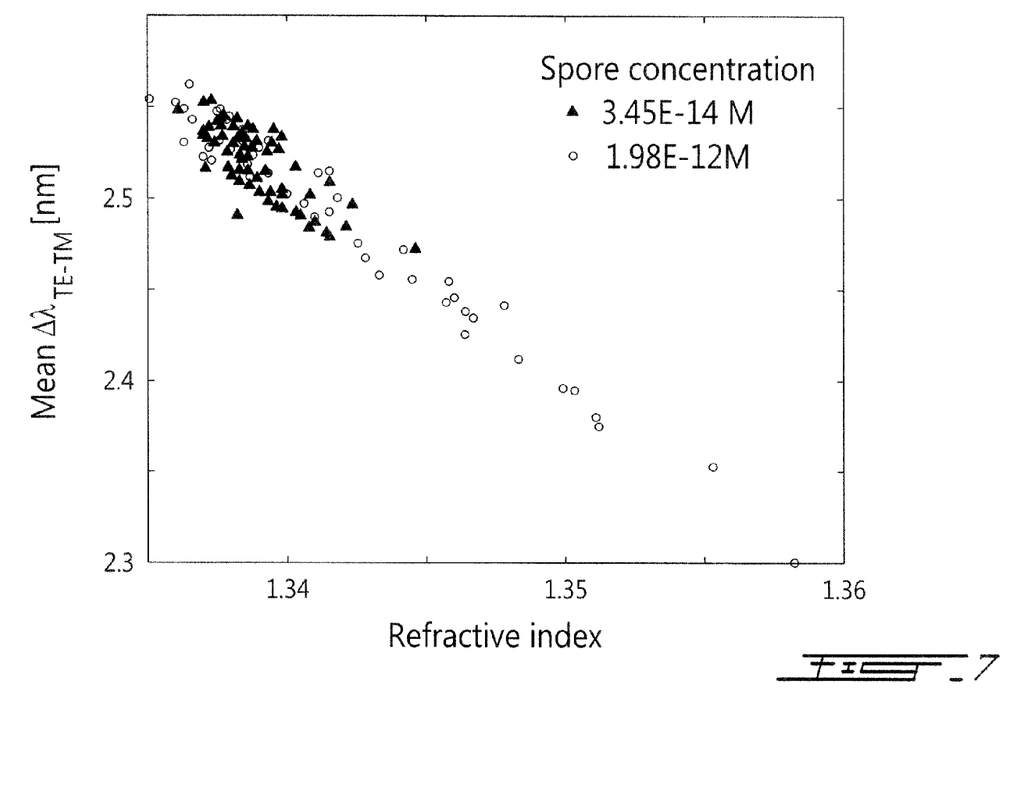
FIG. 7 is a graph of the apparent refractive index and the calculated mean TE-TM spacing of 50 microsphere sensor measurements for two different concentrations of $B.$ $globigii$ spores, i.e. 3.45E-14 M and 1.98E-12 M, wherein the data for the higher concentration of spores stretch further into the lower right and wherein it was assumed that each point corresponds to a greater number of spores adsorbed on the corresponding microsphere.

To start quantifying the detection of *B. globigii* spores, we use the control sample as a reference and assume that no solvent contamination occurs. The threshold for biodetection is set at 3 standard deviations from the average refractive index and mean TE-TM spacing values of the control sample. This threshold is represented by the gray ellipse in FIG. 6. All points lying outside this threshold are considered as detection events. When there are more spores in the solution, a larger fraction of the microsphere population will capture them corresponding to an increasing number of detection events. This relationship, as shown in the inset of FIG. 6, was measured using the solutions of known spore concentration. It can then become a quantitative reference curve to evaluate unknown spore concentrations with a measure of the biodetection event percentage. As the concentration of spores in solution increases, the detection event ratio will approach unity, but the data points should continue to move along the (m0, mean $\Delta\lambda_{TE-TM}$) correlation curve. Hence, the sensor could still yield a reliable measure of spore concentration using the average of the apparent refractive index values instead, since this average will increase as the cloud of data points moves.

Coating Microspheres with cQDs:

It is desirable to extend the fluorescence range of the microspheres, since the numbers of WGMs available for fitting and statistical analysis will be increased. This can be accomplished with cQDs of different emission colors mixed together and coated on the microspheres to provide the light source coupling into the WGMs. Other improvements should ensue from replacing embedded organic fluorophores with cQDs, such as (1) broader absorption spectra giving more freedom for the choice of excitation wavelength; (2) better visibility of the WGMs, since cQDs located only on the microsphere surface have a better overlap with the evanescent field of the WGMs, thus increasing the coupling and reducing the spontaneous fluorescence background; and (3) it becomes possible to use silica microspheres with less permeability to the solvents and less internal light scattering than polystyrene, hence improving the Q factor. The cQDs were prepared following an organo-metallic synthetic protocol, then were made water soluble by encapsulating them in an amphiphilic polymer, and finally were coated on the microspheres with a layer-by-layer (LbL) procedure. Briefly for the encapsulation, the cQDs were transferred from chloroform to water in presence of soluble poly(styrene-co-vinyl benzyl chloride) copolymer previously quaternized with N,N dimethylhexadecylamine. The surface charge making the cQDs polar, hence water soluble, is provided by quaternary ammonium ions linked to the polymer. Since this charge is positive, the cQD coated microspheres will be ready to attract negatively charged analytes. For the LbL coating method, the first step consisted of the alternate adsorption of poly(etyleneimine) (PEI) and polyacrylic acid salt (PAA) onto polystyrene microspheres in phosphate buffer saline solution. This primer layer provided a negatively charged microsphere surface. In a second step, the positively charged cQDs were electrostatically attracted on the negatively charged carboxyl (COO—) groups of PAA on the microspheres.

Figure 4:
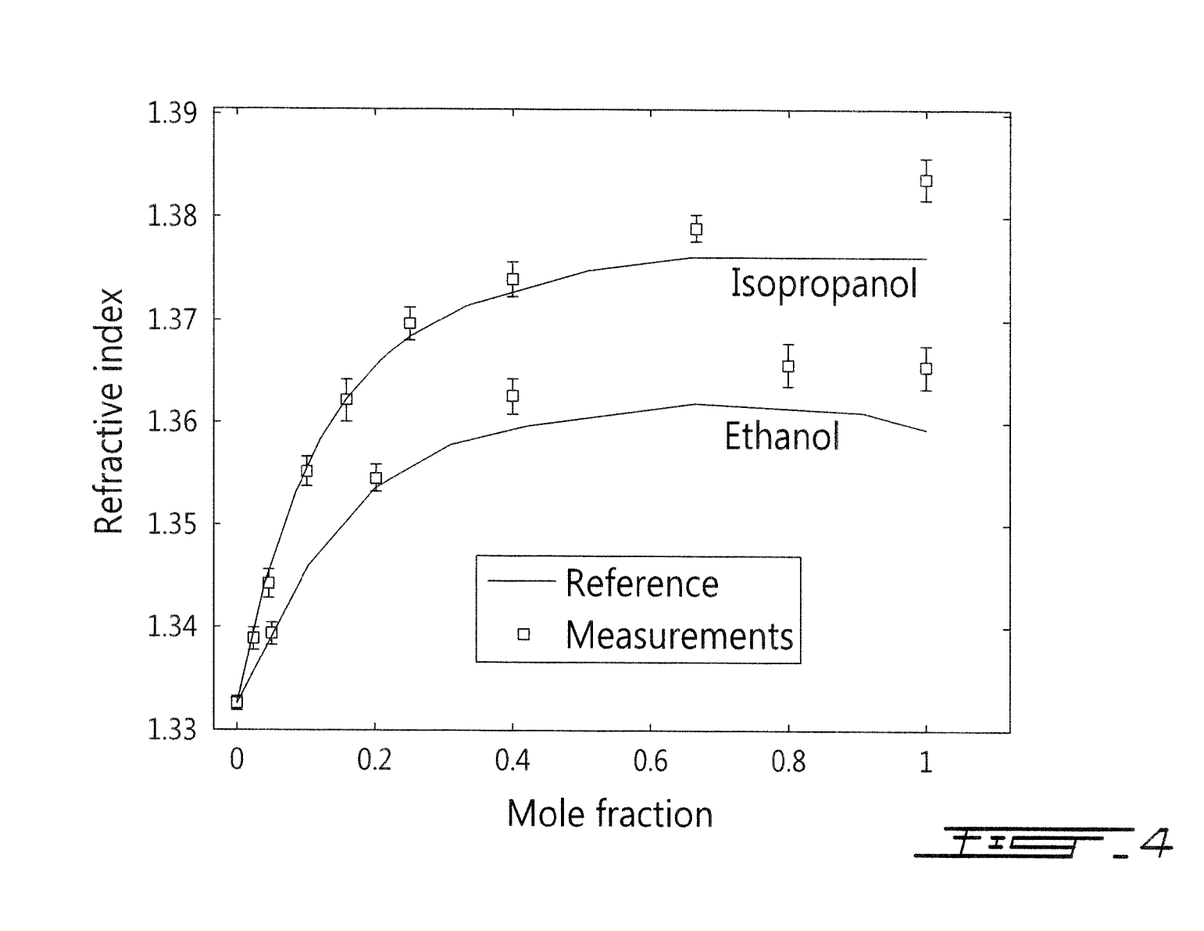
FIG. 4 is a graph showing the refractive index of different isopropanol and ethanol concentrations in water measured with our analysis of multiple WGMs, spectra were acquired and analyzed for 50 fluorescent microspheres at each concentration, each point corresponding to the average of the refractive index distribution, the uncertainties representing the standard deviation of each distribution and the solid lines representing the measures taken with known optical methods.

Clear WGMs are observed in the fluorescence spectrum of green CdSe/ZnS cQDs coating≈3 µm microspheres. Their spectral range of ≈100 nm is already slightly larger than the emission range of the commercial microspheres previously studied even if this particular synthetic batch of cQDs was not optimized to cover a large emission bandwidth. Indeed, relaxing the growth conditions would easily yield more diverse cQD sizes and the overall emission spectrum would be broadened, since the cQD emission wavelength typically changes with their size. In upcoming experiments, we will coat the microspheres with mixed batches of cQDs emitting different large-bandwidth colors to broaden the spectrum even more, but here we are comparing the WGMs with those from the commercial microbeads on roughly the same green spectral range. We first observe the expected decrease in spontaneous fluorescence background compared to the spectrum of the commercial microbeads. FIG. 4($a$). This confirms the location of the cQDs near the microsphere surface, they most likely stayed within the charged polymer layers without diffusing significantly. The EMT should thus be modified to account for the emitting dipoles that are now only in a spherical shell around the microsphere. Another observation about the WGMs is their low Q factor of ≈200 associated with a wide spacing between the modes. This is not entirely attributed to the cQD coating, since the ≈1.5 µm microsphere radius is significantly smaller than the ≈4.95 µm radius of the commercial microspheres. Such a small microsphere radius was chosen to improve the detection sensitivity, since the WGM evanescent field leaks further out into the surroundings to be probed. However, as was mentioned herein above, a compromise should be made between the Q factor and the free spectral range between the azimuthal l-numbered modes. With the current ≈100 nm-wide spectra, the small number of WGMs will not be sufficient to make our fitting algorithm converge to a single absolute $\chi^2$ minimum. This issue will be addressed by wider spectra emitted from multicolored cQDs coating slightly bigger microbeads.

A last observation, which was not seen in the case of the commercial microbeads, is the presence of tiny peaks within each azimuthal TE and TM mode more clearly. In fact, a large drop by a factor 10 of the Q factor for the cQD-covered microbeads compared to the commercial ones is surprising and is likely to come from the apparition of the extra peaks in addition to the broadening of the azimuthal l-modes for smaller microspheres. This suggests the presence of an elongation breaking the symmetry of the microspherical cavity. Indeed, when the microbeads are perfectly spherical, the angular dependence of the electromagnetic field is symmetric and it yields a series of polar m-modes degenerate in wavelength for each l-mode. The extra peaks in the experimental spectra are presumably the polar modes no longer degenerate due to a small elongation e=$(r_p-r_e)/a$ where $r_p$ is the polar radius and $r_e$ the equatorial radius of the resulting spheroid. The polar m-modes can be spread over more than a nanometer by elongation values as small as 0.005, which are even easier to reach in the case of microbeads with smaller radii a. The possible origins of this elongation here could be an uneven LbL polymer and cQD coating or simply the microbeads themselves if they were already distorted. Future work on cQD-covered microbeads will focus on raising the Q factor by improving the cQD deposition methods and the choice of material for the microspheres (silica, melamine formaldehyde, etc.) as well as adjusting our fitting algorithm for the modified EMT and for larger WGM spectra.

The results obtained for a polydisperse population of free floating fluorescent microspheres show that it is indeed possible to determine at the same time the microsphere size and its surrounding refractive index when multiple WGMs are used in the analysis of the emission spectrum. We have thus developed a calibration-free refractive index sensor and tested it on different water-alcohol solutions. A precision of $3\times10^{-4}$ in refractive index measurement was achieved and could be improved, since it is proportional to the number of spectra acquired and to the spectral range used. We also demonstrated the versatility of our method by applying it to biodetection. $B.$ $globigii$ spores were successfully detected with two different parameters in the WGM analysis, i.e., the apparent refractive index and the calculated mean TE-TM mode spacing; the correlation between them was also verified. This biodetection method is easy to implement with a small number of preparation steps and only requires low-cost equipment. A freely moving population of microsphere sensors will also increase analyte capture efficiency compared to a static sensor made of immobilized microspheres or other surface-based detection methods. These features combined with the systematic character of our method offer a possibility for automatization in real time, especially when the microsphere sensors are coated with colloidal quantum dots of various colors to improve the WGM visibility and provide a wide fluorescence spectrum.

It is noted that steps of the methods described herein may be implemented on a computer or any other device or apparatus adapted for processing data.

The embodiments described above are intended to be exemplary only. The scope of the invention is therefore intended to be limited solely by the appended claims.

What is claimed is:

1. A detection method using whispering gallery modes, the detection method comprising:
  providing microspheres floating in a solution under test, the microspheres having varying external refractive index and varying radius;
  exciting fluorescence of at least one of the microspheres by exposure to excitation light;
  measuring a fluorescence spectrum of the at least one fluorescent microsphere, said fluorescence spectrum comprising multiple whispering gallery modes;
  obtaining a set of predetermined fluorescence spectra corresponding to the at least one fluorescent microsphere;
  identifying a matching fluorescence spectrum of the set which more closely matches the measured fluorescence spectrum; and
  comparing the matching fluorescence spectrum of the set to the measured fluorescence spectrum.

2. The detection method of claim 1 further comprising detecting analytes attached to the microspheres in the solution upon determining that the measured fluorescence spectrum differs from the matching fluorescence spectrum.

3. The detection method of claim 2 wherein the analytes are biological molecules.

4. The detection method of claim 2 wherein the analytes are micro-organisms.

5. The detection method of claim 1 further comprising detecting a liquid substance blended in the solution under test upon determining that the measured fluorescence spectrum differs from the matching fluorescence spectrum.

6. The detection method of claim 1 wherein microspheres include at least two sets of microspheres, each set having a characteristic fluorescent spectrum.

7. The detection method of claim 6 wherein each one of the at least two sets of microspheres is functionalized for a different analyte.

8. The detection method of claim 1 further comprising determining at least one parameter corresponding to the at least one fluorescent microsphere using an external refractive index corresponding to the matching fluorescence spectrum; and determining a presence of an analyte attached to the at least one fluorescent microsphere as a function of at least one parameter and a predetermined distribution of refractive index of said solution under test.

9. The detection method of claim 8 wherein the at least one parameter is an apparent external refractive index.

10. A detection method using whispering gallery modes in microspheres floating in a solution under test, the detection method comprising:
exciting at least one fluorescent microspheres functionalized for targeted analytes and floating in said solution under test by exposing it to excitation light;
measuring a fluorescence spectrum of said one of said fluorescent microsphere, said fluorescence spectrum comprising multiple whispering gallery modes;
comparing the measured fluorescence spectrum with a set of predetermined fluorescence spectra, fluorescence spectra of the set corresponding to a various known external refractive index and various known radius of microspheres, in order to identify a matching fluorescence spectrum of the set which more closely match the measured fluorescence spectrum;
determining an apparent external refractive index corresponding to said one of said fluorescent microspheres using said known external refractive index corresponding to the matching fluorescence spectrum; and
determining a presence of targeted analytes attached to said one of said fluorescent microspheres as a function of at least the apparent external refractive index and a predetermined distribution of refractive index of said solution under test.

* * * * *